(12) United States Patent
Breen

(10) Patent No.: US 7,502,641 B2
(45) Date of Patent: Mar. 10, 2009

(54) METHOD FOR IMAGING THE RELATIVE MOTION OF SKELETAL SEGMENTS

(75) Inventor: Alan Breen, Christchurch (GB)

(73) Assignee: AECC Enterprises Limited, Bournemouth (GB)

( * ) Notice: Subject to any disclaimer, the term of this patent is extended or adjusted under 35 U.S.C. 154(b) by 168 days.

(21) Appl. No.: 10/520,489

(22) PCT Filed: Jul. 8, 2003

(86) PCT No.: PCT/GB03/02934

§ 371 (c)(1),
(2), (4) Date: Jan. 7, 2005

(87) PCT Pub. No.: WO2004/004570

PCT Pub. Date: Jan. 15, 2004

(65) Prior Publication Data

US 2005/0259794 A1    Nov. 24, 2005

(30) Foreign Application Priority Data

Jul. 9, 2002 (GB) .................................. 0215848.3
Nov. 11, 2002 (GB) .................................. 0226264.0

(51) Int. Cl.
*A61B 5/05* (2006.01)
*A47B 13/08* (2006.01)
(52) U.S. Cl. .................... 600/415; 5/601; 600/410; 600/436
(58) Field of Classification Search ........... 600/410, 600/415, 422; 5/601
See application file for complete search history.

(56) References Cited

U.S. PATENT DOCUMENTS

| 5,090,042 A | 2/1992 | Bejjani et al. |
| 5,099,859 A | 3/1992 | Bell |
| 5,320,640 A | 6/1994 | Riddle et al. |
| 5,445,152 A | 8/1995 | Bell et al. |

(Continued)

FOREIGN PATENT DOCUMENTS

EP    0 804 032 A2    10/1997

(Continued)

OTHER PUBLICATIONS

Breen et al., "Quantitative Analysis Of Lumbar Spine Intersegmental Motion," *European Journal Of Physical Medicine And Rehabilitation*, 1993, vol. 3, No. 5, pp. 182-190.

(Continued)

*Primary Examiner*—Eric F Winakur
*Assistant Examiner*—Helene Bor
(74) *Attorney, Agent, or Firm*—Cecily Ann O'Regan; Wilson Sonsini Goodrich & Rosati

(57) ABSTRACT

Methods and apparatus for measuring the movement of bones during joint motion in a subject using a motion table, an imaging device, and software program for tracking, calculating and graphing the results of the motion study. The apparatus is a motion table used to control the movement of the subject while an imaging device captures images during that movement. The images are analyzed using a computer software program that tracks the individual bones that make up the joint, calculates their relative movements, and graphically displays the results as a function of time.

24 Claims, 8 Drawing Sheets

Passive Motion Platform - Side Elevation

U.S. PATENT DOCUMENTS

| | | | |
|---|---|---|---|
| 5,772,595 A | | 6/1998 | Votruba et al. |
| 5,810,006 A | * | 9/1998 | Votruba et al. ............... 600/415 |
| 5,891,060 A | * | 4/1999 | McGregor et al. ........... 600/595 |
| 5,899,859 A | * | 5/1999 | Votruba et al. ............... 600/415 |
| 5,931,781 A | * | 8/1999 | De Boer ....................... 600/415 |
| 5,954,674 A | * | 9/1999 | Fuhr ............................ 600/594 |
| 6,141,579 A | * | 10/2000 | Bonutti ........................ 600/415 |
| 6,697,659 B1 | * | 2/2004 | Bonutti ........................ 600/407 |
| 7,117,027 B2 | * | 10/2006 | Zheng et al. ................. 600/426 |
| 7,158,661 B2 | * | 1/2007 | Inoue ........................... 382/128 |
| 7,243,387 B2 | * | 7/2007 | Schindler ......................... 5/601 |
| 2003/0225327 A1 | * | 12/2003 | Willen et al. ................. 600/415 |

FOREIGN PATENT DOCUMENTS

| | | |
|---|---|---|
| EP | 1519681 B1 | 11/2006 |
| JP | 7284020 | 10/1995 |

OTHER PUBLICATIONS

Breen et al., "An Image Processing Technique For The Radiographic Assessment Of Vertebral Derangements," *The Journal Of Photographic Science*, 1989, vol. 37, pp. 131-132.

Breen, "Integrated Spinal Motion: A Study Of Two Cases," *The Journal Of The CCA*, 1991, vol. 35, No. 1, pp. 25-30.

Breen, "Spine Kinematics: A Digital Videofluoroscopic Technique," *Journal Of Biomedical Engineering*, 1989, vol. 11, pp. 224-228.

Breen, "An Image Processing Method For Spine Kinematics-Preliminary Studies," *Clinical Biomechanics*, 1988, vol. 3, pp. 131-132.

Breen, et al., "Image Presentations For Spinal Kinematic Analysis Using Digital Videofluoroscopy," *Third International Conference On Image Processing And Its Applications*, 1989, pp. 343-347.

Lee et al., "Development And Validation Of A New Technique For Assessing *Lumbar Spine Motion*," *Spine*, 2002, vol. 27, pp. E215-E220.

Humphreys et al., "Incremental Lumbar Spine Motion In The Coronal Plane: An Observer Variation Study Using Digital Videofluoroscopy," *European Journal Of Chiropractic*, 1990, Vo.. 38, pp. 56-62.

Karhu, et al. Kinematic magnetic resonance imaging of the upper cervical spine using a novel positioning device. Spine. Oct. 1, 1999;24(19):2046-56.

Breen, et al. Lumbar spine motion palpation compared with objective intervertebral motion analysis: preliminary findings. European Journal of Chiropractic. 2002; 50, 27-32.

* cited by examiner

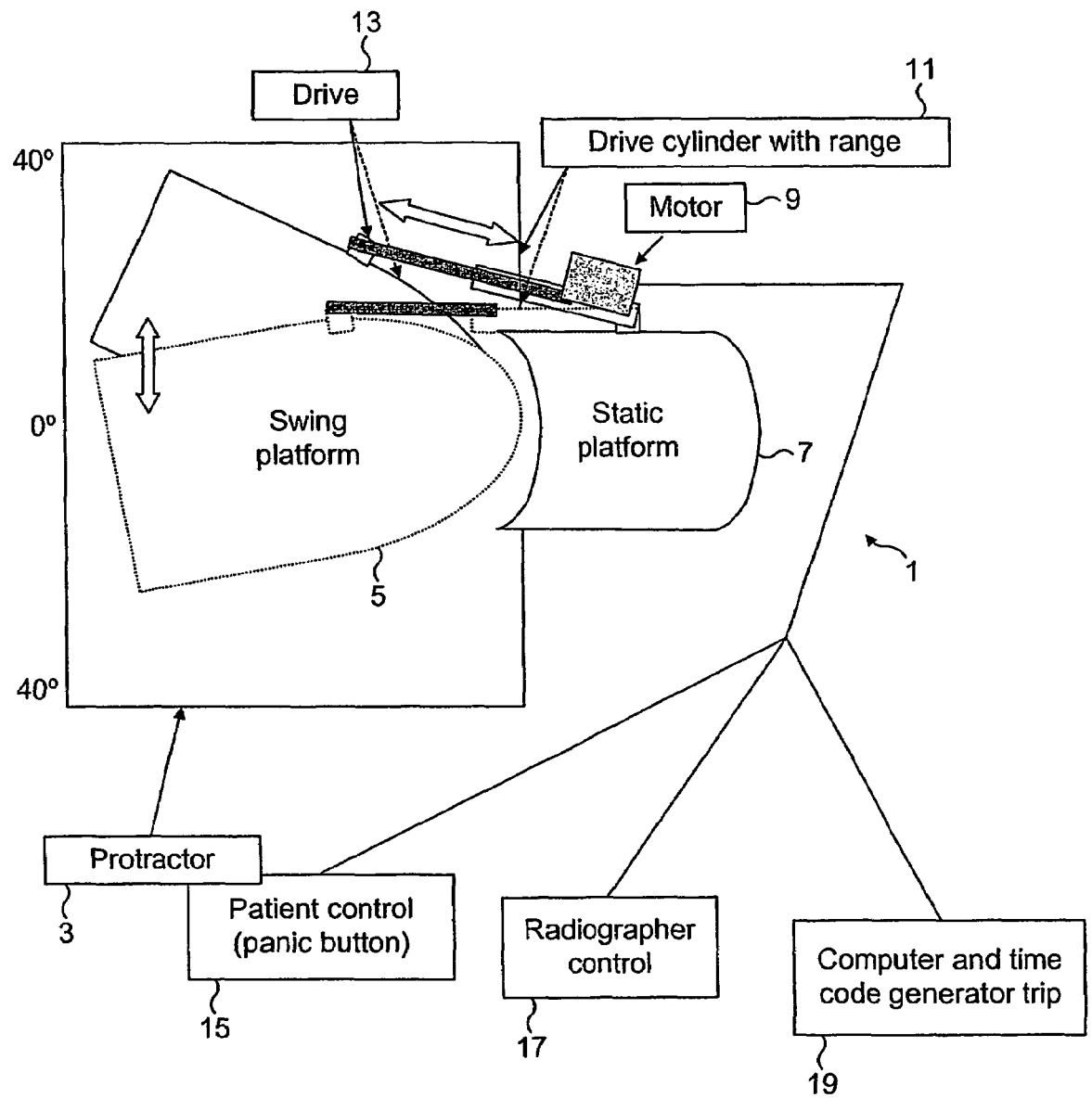

Passive Motion Platform - Side Elevation

Linked Components of the System

X-ray image of a vertebra with implanted surgical Screws and rods with outline of templates denoting areas of bone image enclosed for automatic tracking

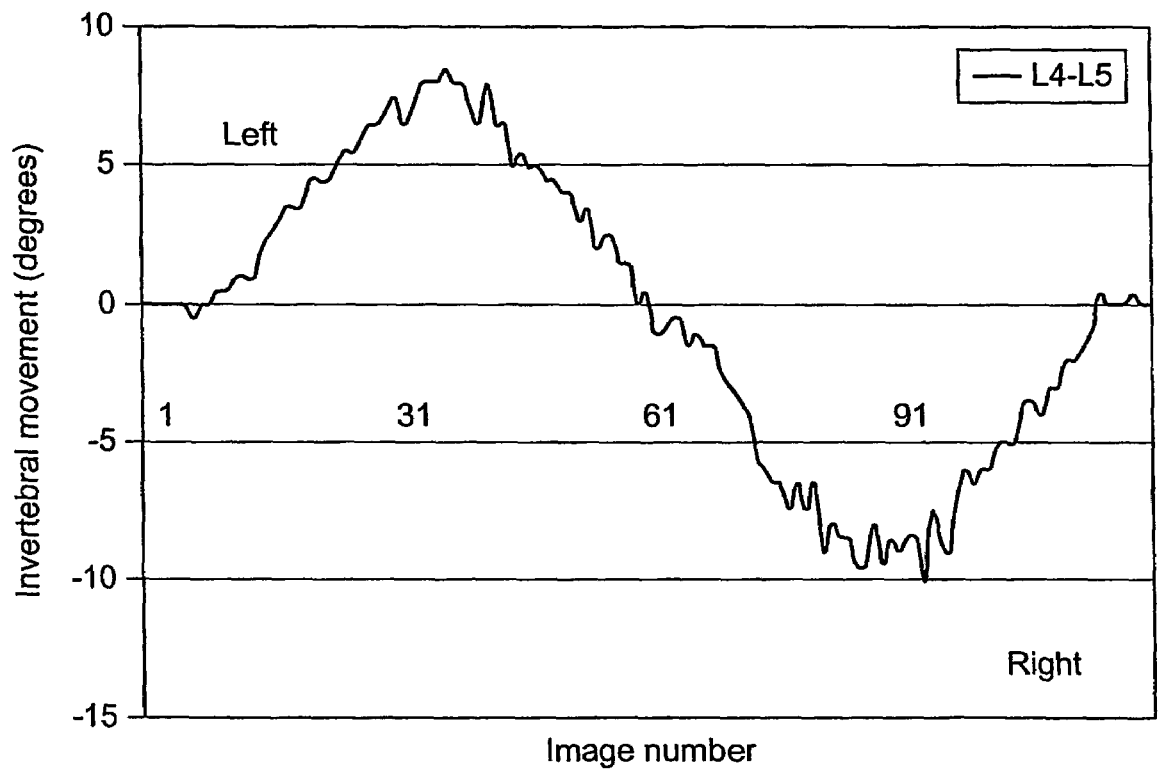

Example of automated tracking results: Average of ten automated registrations of a series of mobile intervertebral loins through a full sidebemding range for 4 vertebrae simultaneously

METHOD FOR IMAGING THE RELATIVE MOTION OF SKELETAL SEGMENTS

CROSS-REFERENCE TO RELATED APPLICATIONS

This application is the U.S. National Stage filing of International Application Serial No. PCT/GB2003/002934 filed Jul. 8, 2003, which claims priority to GB 0215848.3 filed Jul. 9, 2002 and to GB 0226264.0 filed Nov. 11, 2002, each of which is incorporated herein by reference in its entirety.

FIELD OF THE INVENTION

The present invention relates to an automated system for monitoring the movement of bones in the skeleton of a subject, with particular reference to the bones in patients after surgery.

BACKGROUND OF THE INVENTION

The skeleton is the support system of land animals and its joints are key to its structural integrity in everyday life. Examining this integrity for the purpose of understanding malfunction in the living organism, without penetrating the surface, has hitherto been an insurmountable problem, preventing accurate diagnosis and informed treatment. This has meant that the functional integrity of joints, especially the spinal joints, could not be assessed in living subjects without resorting to invasive procedures. Spinal fusions, often a last resort for intractable back pain, could not be inspected for their success without revision surgery, and suspected disruption of ligaments could not be objectively assessed.

Attempts to overcome this difficulty by placing measuring devices on the surface of body segments, and recording their displacements during movement of the body were unsatisfactory because it was surface (skin) rather than bone motion that was recorded—especially in relation to the segments of the spine. The use of plain X-rays was also unsatisfactory because only the beginning and end of the motion could be recorded without giving a prohibitive radiation dose. Attempts involving cineradiography and videofluoroscopy allowed the whole range of motion to be seen on film or videotape, but not measured. Furthermore, marking a sufficient number of the images in a motion sequence manually, in pursuit of such measurement, was too laborious to support a method for use in clinical settings. See, for example, U.S. Pat. No. 5,090,042. Additionally, voluntary motion of joints adds the confounding factor of the stabilising influence of the muscles, concealing any abnormality of the joint ligaments or other passive elements, notably the intervertebral discs.

There is, therefore, a need for a system that provides a means for producing real-time image generation of the motion of the bones in a subject than can objectively measure the functional integrity of joint tissues with the minimum of invasiveness.

SUMMARY OF THE INVENTION

The present invention makes it immediately possible to use x-ray intensifier technology, or its successors (e.g. real-time magnetic resonance or other imaging), to carry out these procedures by objectively measuring the functional integrity of joint tissues with a minimum of invasiveness. Its immediate application is to the detection of failed spinal fusions, avoiding the necessity for a second operation to inspect the integrity of the original graft.

BRIEF DESCRIPTION OF THE DRAWINGS

The invention will now be further described by way of reference to the following Figures which are provided for the purposes of illustration only and are not to be construed as being limiting on the invention. Reference is made to a number of Figures in which:

FIG. 1(a) shows the passive motion platform in its top elevation where it is sited atop an X-ray table.

FIG. 3(a) shows a line graph in which in which is shown the results of tracking the angular motion of one intervertebral linkage (2 consecutive vertebrae) through a full side-bending range. The x-axis denotes the number of increments of motion between images registered by the tracking system. The y-axis denotes the magnitude of the angles between the one pair of vertebrae in side-bending (coronal plane motion) with, by convention, left side-bending being the positive direction and right side-bending the negative.

DETAILED DESCRIPTION OF EMBODIMENTS

Figure 1B:
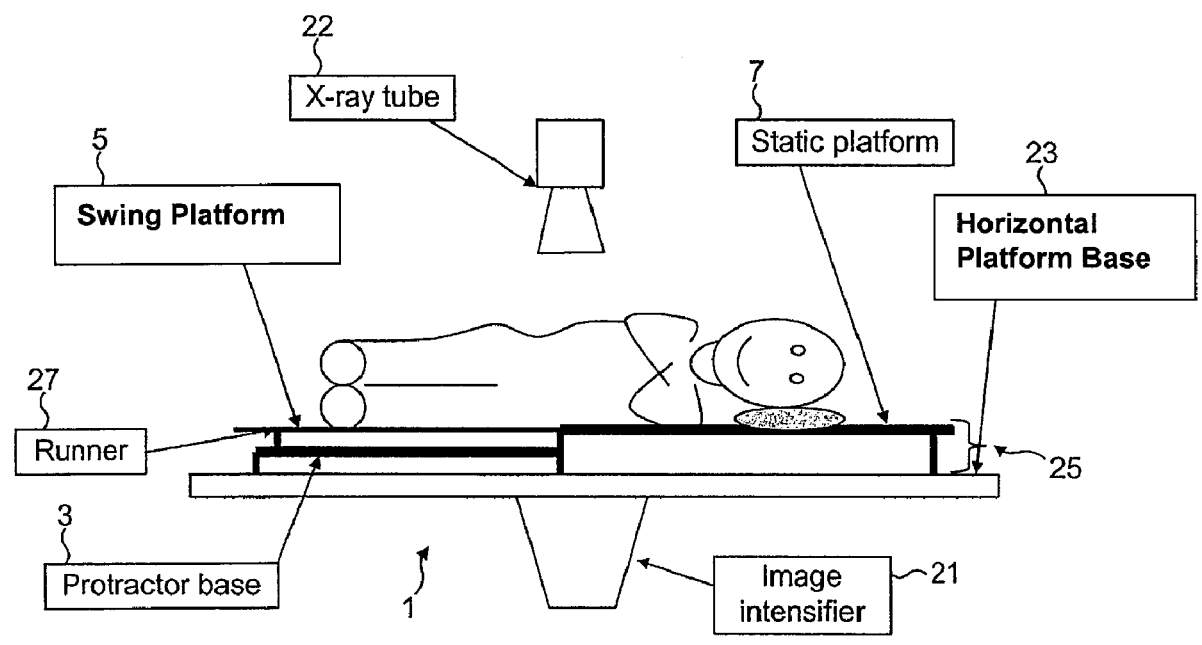
FIG. 1(b) shows the passive motion in its side elevation as would be viewed from the X-ray console with a patient undergoing the imaging of vertebral joint motion in the lower spine in the sagittal plane. (Turning the patient to the supine position would allow side-bending, or coronal plane, motion.)

According to a first aspect of the invention, there is provided apparatus for the measurement of skeletal joint motion in a subject comprising:

(a) a passive motion device which comprises a horizontal platform base and a horizontal passive motion platform composed of a horizontal static platform which is rigidly connected to the upper lateral surface of the platform base and a horizontal laterally movable platform which is flexibly connected to the static platform or to the upper surface of the platform base, in which the static platform is adjacent to the laterally movable platform which together both form the passive motion platform, in which the movement of the laterally movable platform is driven by a motor attached to the platform base where movement of the laterally movable platform is achieved by means of a control arm that operably connects the laterally movable moveable platform to the motor;

(b) an imaging device;

(c) a processing system which comprises a computer incorporating a means for real time digital sampling of images of the moving joints, means for recording time code and data from the passive motion platform; means for storage of these images at high resolution; means for recognising templates attributed to individual bones and tracking these automatically using cross-correlation functions; and means for geometric transformation of the positional data to graphically display their relative motion over time.

The apparatus for the measurement of skeletal joint motion allows for the accurate measurement of movement in skeletal structures through the operation of the passive motion device which permits the joints to be moved at a controlled rate within patient tolerances and through a range appropriate for measurement using the means contained within the processing system.

The horizontal platform base may be a table or similar construction to permit stable operation of the device. Suitable tables include tables used for X-ray purposes or imaging purposes in a medical environment.

The passive motion platform is composed of a horizontal static platform and a horizontal laterally movable platform. The static platform can be securely fixed to the platform base through its lower lateral surface. The static platform co-operates with the laterally movable platform so as to provide a horizontal surface on which a patient for observation may be positioned.

The laterally movable platform may be flexibly connected to the static platform or to the upper surface of the platform base so as to permit movement of the movable platform in a horizontal plane. The moveable platform or swing platform may be moved through the action of a motor attached to the platform base. The movement of the movable platform may describe an arc sufficient to cause movement of the body of the patient to be observed. In some embodiments of the invention, the laterally movable platform may be superposed or placed on a support which lies on the upper surface of the platform base. Such a support may assist in stabilising the motion of the movable platform in use. Since the rotation of the laterally movable platform may be rotation around a fixed point, the support may take the form of an arc (or circular segment), may be a protractor.

The movement of the laterally movable platform is controlled by a motor attached to the platform base that acts through a control arm. The motor can be hand-operated or powered by electricity. The control arm may be composed of a drive cylinder and a drive rod. Preferably, the drive cylinder has a means for setting the range of movement of the movable platform. The motor may be suitably controlled from behind the x-ray console.

The imaging device is preferably an X-ray tube and image intensifier with dosage control or a magnetic resonance scanner capable of real-time imaging of the joint being examined or any other imaging device capable of providing adequately resolved images.

The processing system as defined above comprises a computer incorporating means for recording and analysing data. Such means for real time digital sampling of images of the moving joints may be image processing software capable of manipulating sequential images, for example IMAGE PRO® image processing software. As an alternative to sampling analogue output form images, the direct sampling of digital format images may also be preferred. Data obtained from the intensifier in a digital format can be accessed by DICOM. The means for recording time code and data from the passive motion platform may be a framegrabber card compatible with the computer image processing software and a time code generator connected to the computer peripherally (for example a FOR.A TGR2000). The images generated may be stored at high resolution on the hard drive of the computer or on a suitable data carrier, for example a compact disc.

The means for recognising templates attributed to individual bones and tracking these automatically using cross-correlation functions may be software for complex mathematical transformations, for example THE MATHWORKS MATLAB® computing software.

The means for geometric transformation of the positional data to graphically display their relative motion over time may be a statistical spreadsheet software program such as MICROSOFT® EXCEL Spreadsheet. This may include averaging repeated trackings to optimise reliability.

The processing system may additionally comprise a means for automatically correcting image dimensions for any distortion contributed by the image intensifier.

In general the computer hardware and image analysis software will have sufficient on-line memory, bit depth and processor speed to sample, affix time code and hold multiple high quality images; sufficient digital storage to retain and replay image sequences; triggering and control linkages to the passive motion and imaging devices; image calibration to correct systematic image distortion; tracking code and algorithms suitable for registering the relative positions of a template placed around a number of adjacent bone images in series' throughout motion sequences; linkage of these outputs to graphical and statistical programs.

The passive motion platform for lower spinal examinations consists of two flat linked surfaces, the static platform and the laterally movable platform, made of radiolucent material on which the subject lies. This is driven by a motorised arm linked to the computer acquisition system during imaging. The tracking of individual bone images accessed directly from an intensifier or other digital imaging output uses much of all the image data for each bone using algorithms based on picture element correlations that can be improved upon by the amount of data available as pixel depth and density. This level of control over image quality is not possible by videofluoroscopic methods, because of the degradation of images caused by using videotape as a storage intermediary. The problems of image degradation by any metallic implants or other artefacts is resolved by using templates to define suitable areas of bone image for tracking and the automated data outputs can be averaged to achieve greater reliability. These are fundamental advances on current surface or imaging methods that do not acquire sufficient data, with sufficient speed or with a sufficient degree of automation and to not measure the responses of the passive holding elements to motion.

It is a central object of the invention to provide an automated system through which the relative motion of images of skeletal structures can be measured in vivo. These range from spinal to limb girdle joints and are suited particularly to the discrimination of movement in joints that have been the subject of surgical fusion. A wider application is, however, the ability of the invention to reveal the motion characteristics of non-fused joints. It is intended that the invention allow moving images of bones to be acquired within a viewing field which addresses an area of interest selected for relative motion assessment with minimal invasiveness over a period of under one minute (if X-rays are used). In the case of X-ray generated images, this incorporates methods for gonadal shielding, filtration and intensifier flare reduction as well as patient stabilisation, procedure rehearsal and ability to stop the procedure if desired. Real-time digital acquisition with superimposed time code and storage of the images for playback and subsequent automated motion analysis is implicit in the invention. The invention outputs numerical or graphical data depicting the relative motion of adjacent bones. These data can be statistically analysed for repeatability and automatically re-calculated and averaged as a means of error reduction. They can also be transformed to display different indices of the motion (e.g. angular change, translational change, or axis of rotation). It is intended that the outputs take the form graphical displays of the motion features of interest for the attention of clinicians.

The apparatus of the invention can be used to measure movement in the skeletal joints of a subject. The subject may be any animal having an internal bony skeleton, preferably an animal with is a mammal. The invention may find greatest utility in the fields of human and veterinary medicine. In veterinary medicine, the method may find use in the treatment of domestic pets as well as to agricultural or zoological animals.

The skeletal joints that can be measured include, but are not limited to the intervertebral linkages of the cervical (neck), thoracic (upper back) and lumbar (lower back) spines In humans, the cervical vertebrae are also known as vertebrae C1 to C7, the thoracic vertebrae as T1 to T12, and the lumbar vertebrae as L1 to L5.

So for example relative motion of lumbar vertebrae L1 to L2, L2 to L3, L3 to L4 or L4 to L5 can be measured simultaneously or separately.

The devices of the present invention differ therefore in certain key respects from those of the prior art. Principally, there is the digitisation of sampled images which provides the enhanced reliability of the methods carried out using the apparatus. The improved reliability is the result of the ability to handle and process large amounts of information which is not seen in the prior art.

According to a second aspect of the invention, there is provided a method for the automated measurement of the relative motion of skeletal structures in vivo, comprising the steps of:

(i) positioning the subject on a passive motion device as defined in accordance with the first aspect of the invention.;
(ii) initiating the imaging procedure of the subject positioned on the passive motion device and collecting image data using an imaging device;
(iii) sampling the data collected by the imaging device into the processing system and superimposing time code on the images;
(iv) tracking templates marked on individual bone segments at the start of the motion sequence;
(v) transforming the results of tracking to reflect the changing spatial relationship between image segments; and
(vi) presenting the output in graphical form.

This aspect of the invention therefore provides methods for acquiring images and analysing the motion of adjacent skeletal structures.

In a preferred embodiment of this aspect of the invention, a calibration step is carried out prior to the method described above. Prior to imaging the skeletal structure, calibration of the computer is achieved by imaging objects of known dimensions in order to allow for any geometric distortion inherent in the imaging device.

The methods may also include a further optional step of measuring the forces involved in the motion of the skeletal structures by measuring the mechanical resistance to the table motion.

Simple adaptation make the method suitable for use with other joints, including those of the cervical spine (neck). The subject is also preferably shielded from x-ray radiation by means of lead shielding material to minimise the dose received.

Methods in accordance with this aspect of the invention can be applied to any joint, safely, reliably and comprehensively, using any imaging system capable of real-time image generation. Such methods can be operated by a radiographer without specific medical training. The methods involve stabilising two adjacent body segments in a mechanical device that moves a joint passively, while briefly imaging this motion in real time. The motion of adjacent bones is tracked by applying digital image processing algorithms to their image sequences and outputting the relative motion data graphically for the inspection of clinicians. Any systematic distortion within the device can be calibrated for and subjected to corrective transformation as a part of processing. Transformation may include dimensions of structures, their rotation, translation and centres of rotation.

Advantages of these methods over the prior art can be summarised as follows. The invention enables the ability to examine side-bending motion, not just flexion-extension in a patient. It is possible to measure many hundreds of data points (typically 100 to 500) rather than the more limited number measurable according to prior art methods that typically can only measure 6 data points. As a result, methods of the present invention enable the ability to analyse segmental motion which occurs at small parts of the range as, for example, in a failed fusion (for example see, FIG. 3 which shows a graph of a patient test with 120 data points). Such data collection requires direct digitisation of the sample images. The ordinary use of videotape is not sufficient as it degrades images so seriously that they cannot be tracked and attempts to devise an imaging technique using videotape remain manual and uneconomic. The use of the passive motion device of the present invention controls the motion of the patient's body and therefore diagnosis depends far more on the device than the coordination abilities of the patient. It is also possible to measure the forces involved in the joint movement by measuring the mechanical resistance to the table motion.

Methods of the present invention therefore enable the objective and accurate measurement of the small movements between vertebrae. In particular, the methods facilitate the investigation of suspected failed spinal stabilisation surgery (pseudoarthrosis) and/or suspected damage to intervertebral soft tissue linkages Such methods permit accurate measurement of the small ranges of segmental motion throughout the range of flexion/extension and side-bending of the spine using fluoroscopy to image the spine in passive motion. The sequential images thus obtained are then stored on disc. Computer software as described herein is used to track the movements of the vertebrae.

The methods can be considered to comprise the following broad elements:

(i) data acquisition—fluoroscopy of the lumbar spine region in flexion/extension and side-bending and digitisation of the images;
(ii) data analysis—registering the positions of the vertebrae and tracking the vertebrae throughout the sequence of images;

(iii) generation of a report with objective evidence (for or against) of the existence of fusion or of pseudoarthrosis in a patient.

The process of data acquisition is undertaken using a device of the present invention as described herein. Patients lie supine on an x-ray table of a passive motion device as defined above for side-bending sequences of movement. Intervertebral motion is therefore passive. This reduces error in analysis due to muscle guarding or unilateral weakness. Patients then lie on their side and the procedure is repeated for flexion/extension. The lower half of the x-ray table (the swing platform) can swing to a maximum of +/−40 degrees of motion.

After labelling the image file with the patient's details the radiographer views the series for quality. The radiographer then uses the first image in the series to mark templates around the bony segments of interest. The first frame of the sequence is selected and the appropriate vertebrae are identified (i.e. for L4/L5 intervertebral angles, L4 and L5 would be marked). This involves marking four reference points (typically the corners) around each vertebral body to make a template. This is done for each vertebral body so as to include as much of the bone as possible with minimal surrounding soft tissue.

Figure 2A:
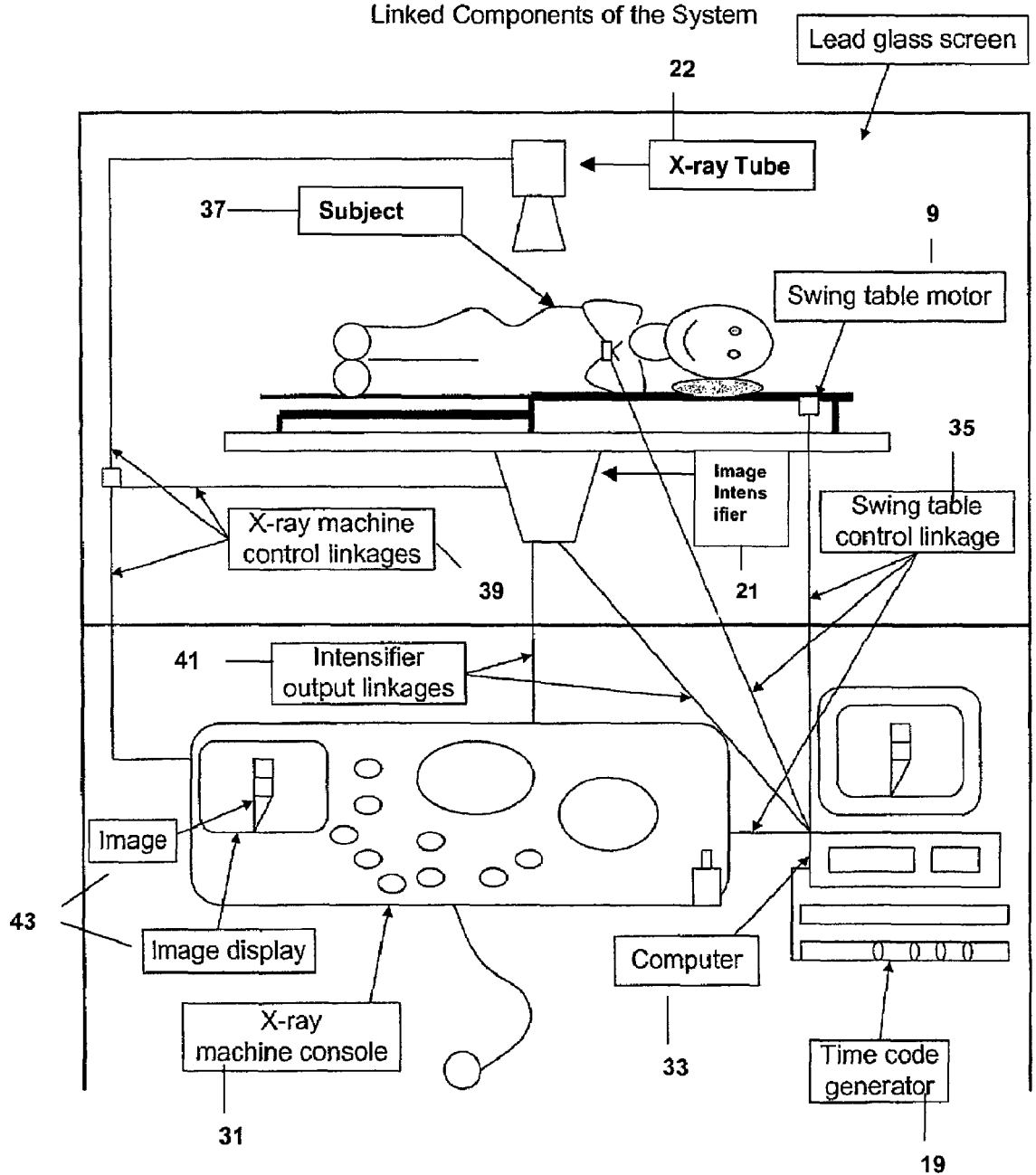
FIG. 2(a) shows the three linked components of the system, being the passive motion platform, the X-ray machine or other imaging device and the computer acquisition and analysis system. The swing table motor (9) is connected via swing table control linkage (35) to the computer (33), the time code generator (19), the patient (37). and the x-ray machine console (31). The x-ray machine console (31) displays the images (43). The x-ray machine control linkages (39) connect the x-ray tube (22). image intensifier (21) and x-ray machine console (31). The intensifier output linkages (41) connect the computer (33). the image intensifier (21) and the x-ray machine console (31).
Figure 2B:
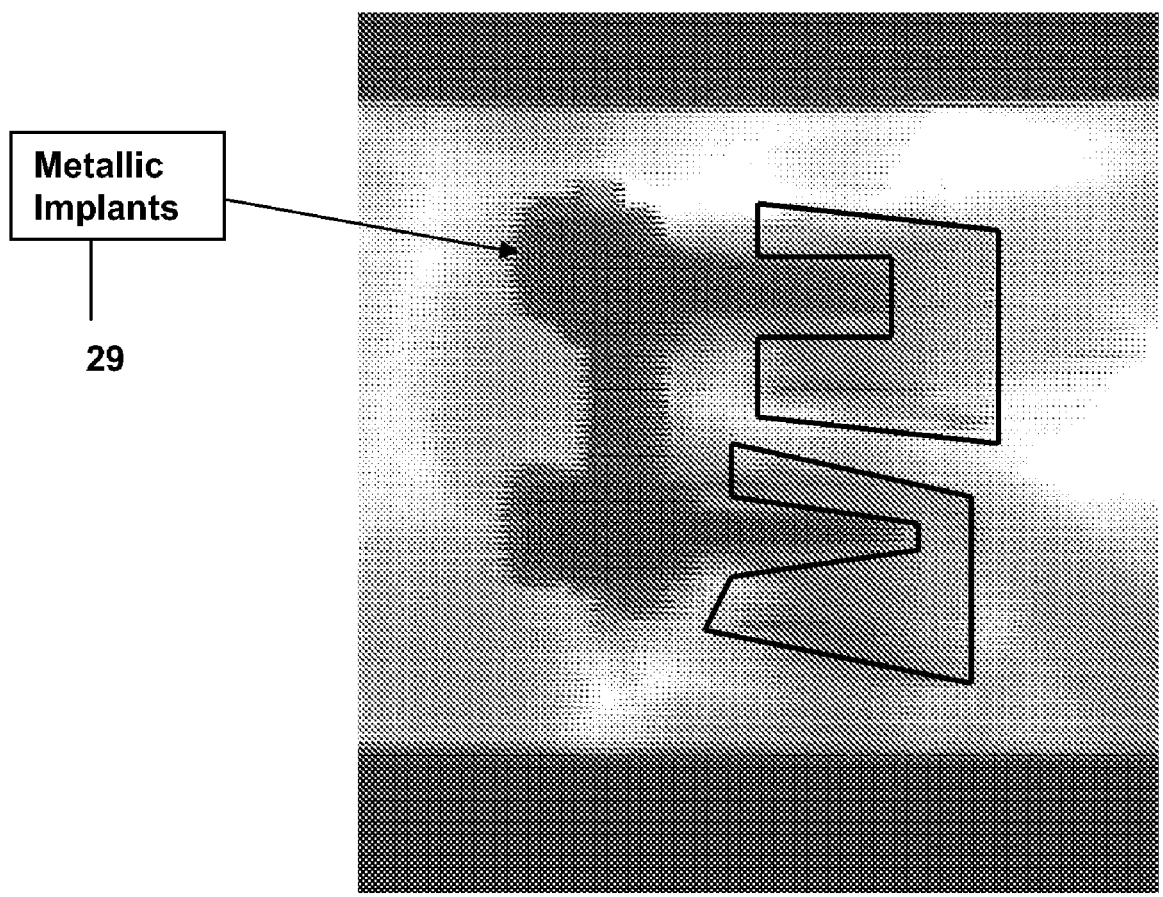

In instances, where there are metallic implants (29) present in the spine (for example as shown in FIG. 2(b)), there may be more than 4 points used to create a template.

The saving of images acquired in the data acquisition process is as follows. The output from the image intensifier may be linked to software in the computer. The images can then be captured in real time (for example 25 frames per second). The maximum possible digital information can then be obtained to increase sensitivity of the vertebral tracking (10 bit depth, 1024 by 1024 pixel density). Each image can be stored as a ".tiff" file and typically there can be 500 images per sequence (or 1000 images per patient).

According to a third aspect of the invention there is provided a method for the diagnosis of a pseudoarthrosis in a subject, the method comprising analysing the relative motion of skeletal structures in the patient according to a method described above.

Preferred features for the third and subsequent aspect of the invention are as for the first aspect mutatis mutandis.

An apparatus for the measurement of skeletal joint motion in a subject in accordance with the present invention is described in FIGS. 1(a) and 1(b). An apparatus is shown which comprises a passive motion device (1) having a horizontal platform base (23) and a horizontal passive motion platform (25). The horizontal passive motion platform (25) is situated on the horizontal platform base (23). The horizontal passive motion platform (25) is composed of a horizontal static platform (7) which is rigidly connected to the upper lateral surface of the platform base and a horizontal swing platform (5) which is flexibly connected to the static platform or to the upper surface of the platform base, in which the static platform is adjacent to the laterally movable platform which together both form the passive motion platform, in which the movement of the laterally movable platform is driven by a motor (9) attached to the platform base where movement of the laterally movable platform is achieved by means of a control arm (11, 13), composed of drive (13) and drive cylinder (11) that operably connects the laterally movable moveable platform to the motor. An imaging device (22, 21) is positioned around the device (1) such that movement of the skeletal joint in the subject can be imaged. The imaging device is suitably an X-ray tube (22) and an image intensifier (21). The device (1) has a protractor base (3) underneath the swing platform (5) which is also provided with a runner (27).

The device (1) also contains linkages to a patient control or panic button (15), radiographer control panel (17) which may be an X-ray console where the imaging device is an X-ray tube, and a computer and time code generator (19).

In use, the device comprises of a static platform and a swing platform. The latter is sited atop a second static platform which also serves as a protractor to indicate the arc of motion which it describes and over whose centre is to be sited the joint of interest. The swing platform articulates with the static platform as a two-dimensional ball-and-socket joint and runs over the static protractor section on low friction wheels (runners). Both the static and the swing platforms are made of radiolucent material and have extensions on which to attach a drive mechanism.

The drive mechanism consists of an electric motor which drives a rod in and out of a cylinder in order to move the swing portion of the table relative to the static platform. This is controlled by a computer chip through which the rate and range of motion can be pre-set and is linked to an ammeter by which the resistance to the motion can be measured.

The motor is operated by a radiographer or assistant with a patient override switch. The motor is also connected to a time code generator such that initiating movement of the platform trips the registration of time code on the images acquired.

The central X-ray beam passes from the X-ray tube to the image intensifier through the joint level of interest during the motion of the swing platform. As the motion progresses the area of interest is kept in the central X-ray beam by the radiographer, and appropriate gonadal shielding and flare reduction is applied.

The conventional path of motion is from the neutral position to full range in one direction, to full range in the opposite direction and back to neutral.

The invention will now be further described by way of reference to the following Examples which are provided for the purposes of illustration only and are not to be construed as being limiting on the invention.

EXAMPLES

Example 1

Imaging of a Patient with Intractable Spinal Pain

Data Acquisition

Typically, a patient with chronic intractable spinal pain will be referred for the investigation. The patient will normally attend the X-ray department as an outpatient and will enter an imaging suite under the direction of a radiographer and an assistant. All components of the device, which is portable, will be in place when the patient enters.

The patient will be familiarised with the action of the passive motion platform by demonstration and then will be helped to lie on it in the prone or supine position. The swing platform will be moved and the patient's acceptance of the motion determined. The range of motion achievable will be decided by discussion and tested without imaging to ensure it is well tolerated. Devices for gonadal protection and the reduction of any intensifier flare will then be placed on the passive motion platform.

The radiographer will centre the level of interest and configure the imaging parameters for the exposure. The assistant will prepare the acquisition system to sample digital images in real time and imprint time code on them.

On a countdown the imaging and digital sampling will begin. The swing section of the passive motion platform will then describe the full range of the motion previously rehearsed with the patient. If the patient wishes to stop the motion, they will press a hand-held control which will return the position to neutral. The acquisition time is normally under 30 seconds.

After the image sequence has been acquired, the patient may be imaged in another plane. If so the same procedure will be followed. At the end of the imaging session the patient is helped from the passive motion platform and leaves.

Data Analysis

After labelling the image file with the patient's details the radiographer views the series for quality. The radiographer then uses the first image in the series to mark templates around the bony segments of interest. The first frame of the sequence is selected and the appropriate vertebrae are identified (i.e. for L4/L5 intervertebral angles, L4 and L5 would be marked). This involves marking four reference points (typically the corners) around each vertebral body to make a template. This is done for each vertebral body so as to include as much of the bone as possible with minimal surrounding soft tissue.

In instances, where there are metallic implants (29) (for example as shown in FIG. 2(b)), there may be more than 4 points used to create a template.

The tracking of images is done automatically using cross-correlation codes and the results held on a spreadsheet as angular or translational motion data, or a transformation thereof. The tracking process is repeated with new templates to determine the repeatability of measurement. High quality images with high repeatability will undergo fewer tracking sequences than lower quality ones. The data from the latter may be averaged over several trackings to achieve reliable results.

The co-ordinates of vertebral movement are then converted into vertebral angles using mathematical software. Intervertebral angles are obtained by subtracting vertebral angles from two adjacent vertebrae.

Each sequence of vertebral motion is analysed five times. In other words, the whole procedure of drawing templates is repeated five times. The mean value for intervertebral angles is calculated and represented graphically as evidence (for or against) conclusive fusion or conclusive pseudoarthrosis.

Figure 3B:
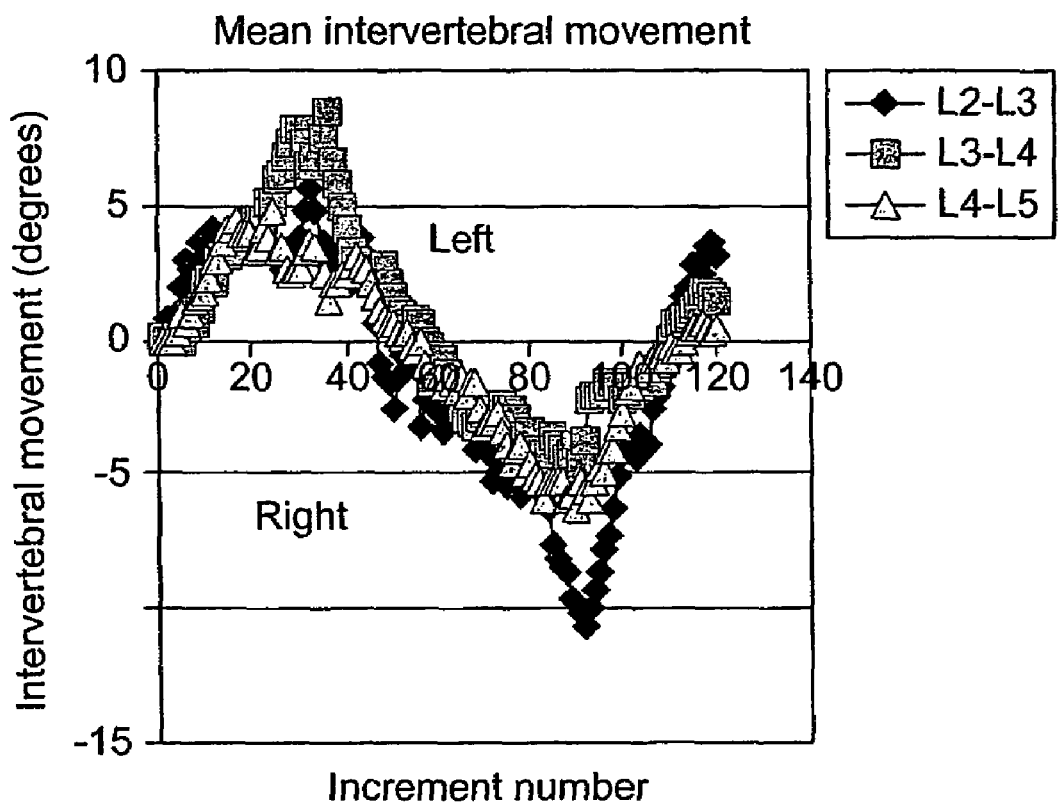
FIG. 3(b) shows an example of automated tracking results for an average of ten registrations of a series of mobile intervertebral joints through a full side-bending range for 4 vertebrae simultaneously (vertebrae L2 to L3, L3 to L4, and L4 to L5).

The results of a typical session are graphically displayed in FIG. 3(a).

Example 2

An Objective Spinal Imaging Assessment of the Integrity of Lumbar Spine Stabilisation Grafts The prospect of a second operative procedure following an apparently unsuccessful spinal fusion is an unwelcome one. The method of the present invention described herein combines sufficiently reduced operator interaction with acceptable error limitation to be operationally useful as a tool for reporting findings about graft integrity for spinal surgeons.

Methods and results: The measurement of lumbar intervertebral coronal and saggital plane motion ii: vivo using this technique is in 3 stages:

Fluoroscopic screening of patients lying on a passive motion table

Co-ordinated real-time digital acquisition of the intensifier images.

Registration of the images of each vertebra by templates which are automatically tracked and whose output is converted to inter-vertebral kinematic parameters and averaged for display and reporting.

Figure 4:
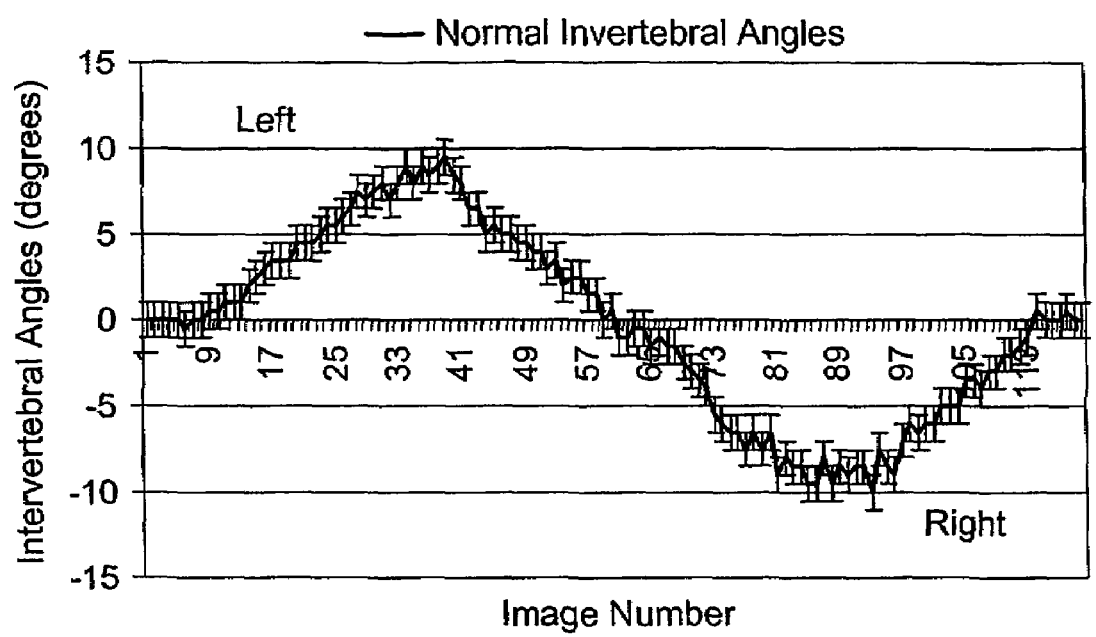
FIG. 4 shows the normal intervertebral angles of vertebrae L4/L5 during passive side-bending motion. The error bars express a 95% confidence interval.

Results are currently displayed as inter-vertebral angles throughout the motion (FIG. 4) that indicate whether or not solid fusion has been achieved, the Instrument Measurement Error is quantifiable and will vary with image quality, but can be improved by averaging. The technology is applicable to any imaging system of sufficient speed and resolution and may, for example, be used with MR in the future.

Figure 5:
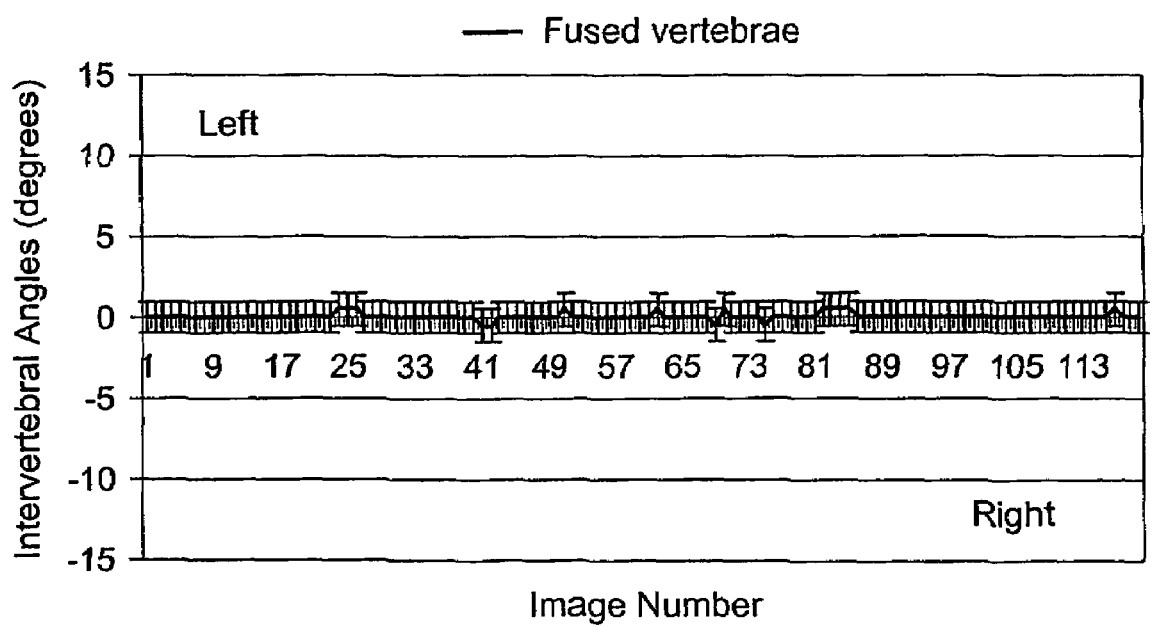
FIG. 5 shows successfully fused vertebrae L4/L5 during side bending motion.
Figure 6:
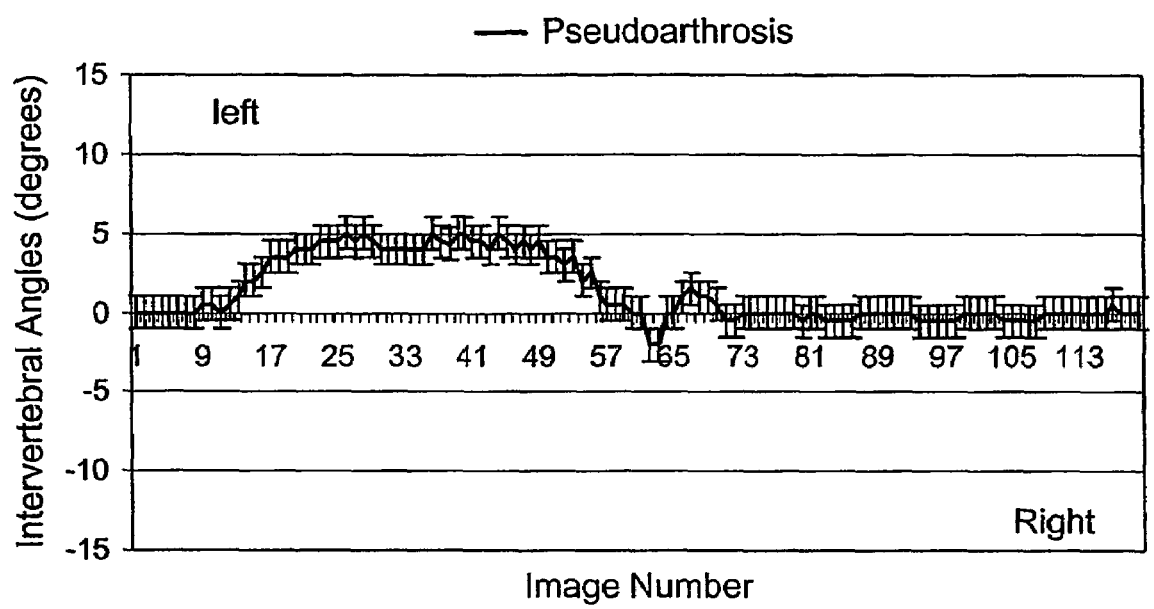
FIG. 6 shows abnormal movement during side-bending in a bone model of vertebrae that have been surgically stabilised. This is indicative of a pseudoarthrosis.
Figure 7:
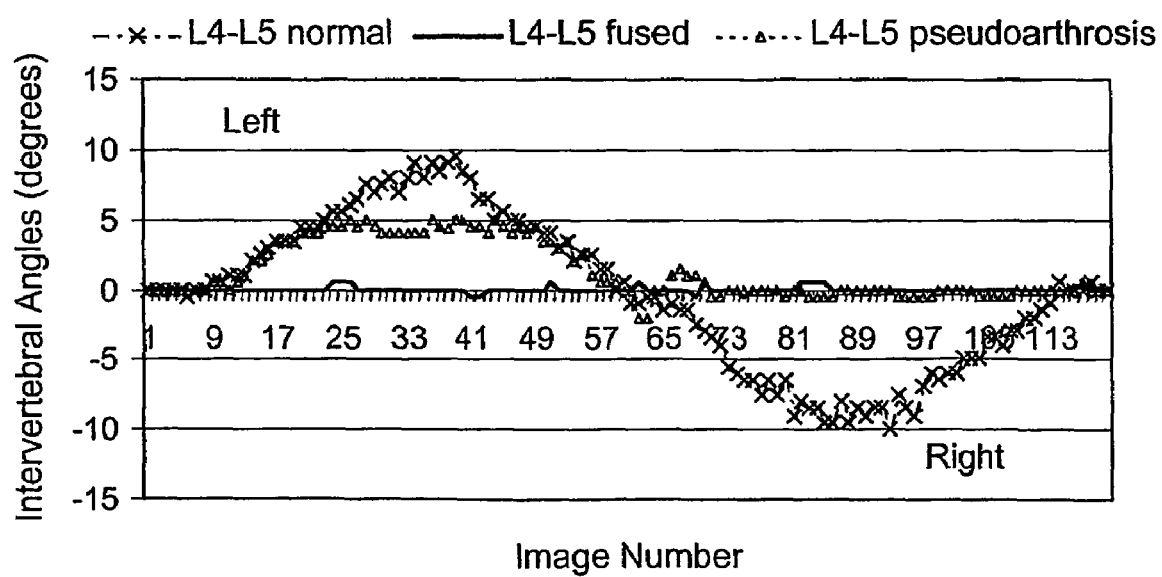
FIG. 7 shows the results from FIGS. 4, 5 and 6 combined which demonstrates the ability of the methods and devices of the present invention to track vertebrae and to calculate intervertebral angles leading to accurate clinical diagnoses.

FIG. 5 shows stable fusion in side bending in a fused bone model using the device. FIG. 6 shows predicted results from a hypothetical pseudoarthrosis. FIG. 7 combines the graphical representations of normal, fused and pseudoarthrosis from FIGS. 4, 5 and 6 for comparison.

The invention claimed is:

1. An apparatus for the measurement of skeletal joint motion in a subject comprising:
   a) a passive motion device for continuously moving a joint which comprises a horizontal platform base and a horizontal passive motion platform composed of a horizontal static platform which is rigidly connected to the upper lateral surface of the platform base and a horizontal laterally movable platform which is flexibly connected to the static platform or to the upper surface of the platform base, in which the static platform is adjacent to the laterally movable platform which together both form the passive motion platform, in which the movement of the laterally movable platform is continuously driven during sampling of images by a motor attached to the platform base where movement of the laterally movable platform is achieved by means of a control arm that operably connects the laterally moveable platform to the motor;
   b) an imaging device; and
   c) a processing system which comprises a computer incorporating a means for real time digital sampling of images of the continuously moving joint during a continuous movement of the joint, means for recording time code and data from the passive motion platform during the continuous movement of the passive motion platform; means for storage of these images at high resolution; means for recognising templates attributed to individual bones and tracking these automatically using cross-correlation functions; and means for geometric transformation of the positional data to graphically display their relative motion over time.

2. An apparatus as claimed in claim 1, in which the imaging device is an X-ray tube and image intensifier with dosage control.

3. An apparatus as claimed in claim 1, in which the imaging device is a magnetic resonance scanner.

4. An apparatus as claimed in claim 1, in which the laterally movable platform is situated on a support which lies on the upper surface of the platform base.

5. An apparatus as claimed in claim 4, in which the imaging device is an X-ray tube and image intensifier with dosage control.

6. An apparatus as claimed in claim 4, in which the imaging device is a magnetic resonance scanner.

7. A method for an automated measurement of the relative motion of skeletal structures in vivo comprising:
   i) positioning a subject on the passive motion device as defined in claim 1;

ii) initiating an imaging procedure of the subject positioned on the passive motion device and collecting image data using an imaging device;

iii) sampling data collected by the imaging device into the processing system and superimposing time code on the images;

iv) tracking templates marked on individual bone segments at the start of the motion sequence;

v) transforming a result of tracking to reflect a changing spatial relationship between image segments; and vi) presenting the output in graphical form.

8. A method according to claim 7, in which the imaging device is an X-ray tube and image intensifier with dosage control.

9. A method according to claim 7, in which the imaging device is a magnetic resonance scanner.

10. A method according to claim 7, in which the laterally movable platform is situated on a support which lies on the upper surface of the platform base.

11. A method according to claim 10, in which the imaging device is an X-ray tube and image intensifier with dosage control.

12. A method according to claim 10, in which the imaging device is a magnetic resonance scanner.

13. A method according to claim 7, in which a calibration step is carried out prior to the method steps i) to vi).

14. A method according to claim 7, in which the relative motion of lumbar vertebrae L3 to L3, L3 to L4 and L4 to L5 are tracked simultaneously or separately.

15. A method according to claim 13, in which the relative motion of lumbar vertebrae L3 to L3, L3 to L4 and L4 to L5 are tracked simultaneously or separately.

16. A method according to claim 7, further comprising the step of comparing the relative motion to a range of motion of skeletal structures of a normal population of people to diagnosis a pseudoarthrosis in a subject.

17. A method according to claim 16, in which the imaging device is an X-ray tube and image intensifier with dosage control.

18. A method according to claim 16, in which the imaging device is a magnetic resonance scanner.

19. A method according to claim 16, in which the laterally movable platform is situated on a support which lies on the upper surface of the platform base.

20. A method according to claim 19, in which the imaging device is an X-ray tube and image intensifier with dosage control.

21. A method according to claim 19, in which the imaging device is a magnetic resonance scanner.

22. A method according to claim 16, in which a calibration step is carried out prior to the method steps i) to vi).

23. A method according to claim 16, in which the relative motion of lumbar vertebrae L3 to L3, L3 to L4 and L4 to L5 are tracked simultaneously or separately.

24. A method according to claim 22, in which the relative motion of lumbar vertebrae L3 to L3, L3 to L4 and L4 to L5 are tracked simultaneously or separately.

* * * * *

UNITED STATES PATENT AND TRADEMARK OFFICE
CERTIFICATE OF CORRECTION

PATENT NO. : 7,502,641 B2  Page 1 of 1
APPLICATION NO. : 10/520489
DATED : March 10, 2009
INVENTOR(S) : Alan Breen It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 208 days.

Signed and Sealed this

Twenty-eighth Day of September, 2010

David J. Kappos
*Director of the United States Patent and Trademark Office*